(12) United States Patent
Cottone et al.

(10) Patent No.: US 6,432,132 B1
(45) Date of Patent: Aug. 13, 2002

(54) EXPANDABLE INTRALUMINAL ENDOPROSTHESIS

(75) Inventors: Robert J. Cottone, Ft. Lauderdale; Gary J. Becker, Miami, both of FL (US)

(73) Assignee: Orbus Medical Technologies Inc., Ft. Lauderdale, FL (US)

(*) Notice: Subject to any disclaimer, the term of this patent is extended or adjusted under 35 U.S.C. 154(b) by 0 days.

(21) Appl. No.: 09/480,672

(22) Filed: Jan. 11, 2000

(30) Foreign Application Priority Data

Jan. 12, 1999 (EP) .............................. 99200067

(51) Int. Cl.[7] .................................................. A61F 2/06
(52) U.S. Cl. ...................................................... 623/1.15
(58) Field of Search .............................. 623/1.15, 1.16, 623/1.17, 1.18, 1.19, 1.2, 1.22

(56) References Cited

U.S. PATENT DOCUMENTS

| | | | | |
|---|---|---|---|---|
| 5,810,872 A | * | 9/1998 | Kanesaka et al. | 606/198 |
| 6,042,597 A | * | 3/2000 | Kveen et al. | 606/198 |
| 6,117,165 A | * | 9/2000 | Becker | 623/1.15 |
| 6,179,868 B1 | * | 1/2001 | Burpee et al. | 623/1.17 |
| 6,190,403 B1 | * | 2/2001 | Fischell et al. | 623/1.15 |
| 6,190,405 B1 | * | 2/2001 | Coluombo et al. | 623/1.15 |
| 6,200,334 B1 | * | 3/2001 | Jang | 623/1.1 |
| 6,264,688 B1 | * | 7/2001 | Herklotz et al. | 623/1.16 |

* cited by examiner

Primary Examiner—David H. Willse
Assistant Examiner—Suzette J. Jackson
(74) Attorney, Agent, or Firm—Young & Thompson

(57) ABSTRACT

An expandable intraluminal endoprosthesis comprises a tubular member having a first and second end and a wall surface disposed between said first and second end. The wall has a first diameter in a first, unexpanded state which permits intraluminal delivery of the member into a lumen of a body passageway, particularly a blood vessel, whilst being capable of acquiring a second diameter in an expanded and deformed state upon the exertion of a radially outwardly extending force to expand the lumen of the body passageway. At least a part of said wall of said tubular member comprises, at least one substantially continuous winding of mutually staggered primary undulations advancing substantially helically along a longitudinal axis of said tubular member. A first primary undulation is connected to an associated second primary undulation by means of a first connection element. A third primary undulation subsequent to said first primary undulation is connected two an associated fourth primary undulation subsequent to said second primary undulation by means of a second connection element. The first and second connection element are themselves mutually connected by means of a connection strut which lies interposed between said primary undulations, at least in said first unexpanded state.

18 Claims, 1 Drawing Sheet

EXPANDABLE INTRALUMINAL ENDOPROSTHESIS

BACKGROUND OF THE INVENTION

The present invention relates to an expandable intraluminal endoprosthesis comprising a tubular member having a first and second end and a wall surface disposed between said first and second end, the wall having a first diameter in a first, unexpanded state which permits intraluminal delivery of the member into a lumen of a body passageway, particularly a blood vessel, and being capable of acquiring a second diameter in an expanded and deformed state upon the exertion of a radially outwardly extending force to expand the lumen of the body passageway. More particularly the invention relates to an expandable intraluminal vascular endoprosthesis which is especially useful for repairing or reconstructing blood vessels narrowed or occluded by a disease. Commonly this kind of medical device is referred to as vascular stent or graft.

Stents are prosthetic devices which are implanted inside a lumen in order to provide support for its wall and to assure an undisturbed flow through the lumen. This is particularly important in the field of angioplasty which is concerned with the repair and reconstruction of blood vessels. In that particular field stents are implanted within the vascular system to reinforce collapsing. partially occluded, weakened, or abnormally dilated sections of blood vessels. More generally, however, stents can be used inside the lumen of any physiological conduit or duct including the arteries, veins, bile ducts, the urinary tract, alimentary tracts, the tracheobronchial tree, a cerebral aqueduct and the genitourinary system. Moreover stents can be used inside lumina of animals besides humans.

Generally two types of stents may be distinguished. First there are self-expandable stents which automatically expand once they are released to assume a permanent deployed, expanded state. The outwardly extending force necessary for its deployment is provided by the spring force of the material used and is accordingly inherently available within the device itself. These stents expand to a defined diameter but are unable to remodel the true vascular anatomy over lengths greater than 2 cm. Their drawback is that the physician needs to place the right device and thereby has to rely on information derived from fluoro and angiographic equipment. However, the same spring force which is responsible for the deployment of the device offers it a relatively large hoop strength, i.e. the ability to withstand radial forces which are exerted on it from the outside.

A second type of stent concerns the so-called balloon expandable stent which generally involves a tubular member capable of receiving a balloon of a balloon-tipped catheter by means of which it may be deployed. A common procedure for implanting a balloon-expandable stent in a blood vessel involves mounting the stent in its unexpanded, crimped state on a balloon-tipped catheter of a suitable delivery system, The catheter is then slipped through an incision in the vessel wall and down the length of the vessel until it is positioned to bridge the diseased or narrowed portion of the vessel. The stent is then expanded with the aid of the balloon catheter against the internal wall of the vessel, This may be done after the vessel has been predilated and it has been determined that a stent is necessary. Alternatively the vessel could be dilated by the stent itself while the latter is expanded by means of the balloon. It both cases the stent will maintain its deployed, expanded form once the balloon is evacuated and the catheter retracted again in order to provide a permanent support for the blood vessel concerned.

A wide overview of vascular stents which are nowadays available is given in the Handbook of Coronary Stents by Patrick W. Serruys et al. of the Rotterdam Thoraxcentre Interventional Cardiology Group. This overview describes at page 21 ff. the so called Palmaz-Schatz™ stent as the gold standard in the field of stents. This stent concerns a number of consecutive slotted tubes of stainless steel which are mutually connected by means of one or more brides. Although this stent is most widely used and tested in practice, having been implanted in over 600000 patients all over the world, it still suffers from a number of drawbacks. The main drawbacks have to do with the stent-to-vessel-ratio uniformity and crimped as well as deployed flexibility. The stent-to-vessel-ratio involves the degree to which the vessel is supported by the stent in its expanded state and should not only be high, but preferably also uniform throughout the length of the stent. However, due to the inevitable bridges between adjacent tubes of the Palmaz-Schatz™ stent, there will be a bare area between adjacent segments of the stent once it has been deployed, giving rise to a decreased and even poor stent-to-vessel-ratio at these locations. The other drawback concerns the rather high rigidity of the stent segments in their crimped and deployed state. As a consequence, the stent has only a limited flexibility which hinders the delivery of the stent to its intended position inside the body. The poor deployed flexibility of this stent gives rise to a straightening of the vessel over segments longer than typically 2 cm which appears to be a primary cause for late term restenosis of the stented area. Typically this may occur about 6 months after the stent implantation.

A balloon expandable stent with a highly uniform stent-to-vessel ratio us well as an excellent flexibility in its crimped state is described at page 63 ff. of the same reference and concerns the Cordis Coronary Stent. This device is composed of a single piece of tantalum (Ta) wire. The wire is wrapped to form a continuous sine wave and helically wound along a longitudinal axis. Both ends of the wire are weld terminated. A similar device was presented at the annual symposium of the Radiological Society of North America (RSNA) 11/95. This peripheral stent embodiment incorporates intermediate welds, patterned through the length of the stent. This device contains adjacent helical turns of the wire which are welded together at adjoining locations and exhibits a highly regular distribution of the wire along the length of the device. Its properties, such as crimped profile and stent-to-vessel ratio, are uniform over its length both in the crimped and deployed states. However, because of its constitution this device offers only a poor design freedom when it comes to tailoring the design to add specific functionality and remove certain drawbacks. Also the internal stress in the device once it has been wound hinders the provision of reliable welds between adjacent turns. Moreover, these welds as well as those to the ends of the wire, remain a weak point especially during expansion of the device.

A balloon expandable stent which combines a high degree of uniformity and flexibility with excellent design capabilities is described in the co-pending European patent application 98201446.6 by applicant. This device features a substantially continuous structure of mutually staggered undulations which has been separated from a tube wall. Said substantially continuous structure comprises at least one pattern which advances substantially helically along a longitudinal axis of said tubular body and comprises connection elements connecting adjacent undulations. The connection elements are an integral extension of the undulations which they connected.

Although the device of said co-pending application provides excellent properties especially regarding its flexibility both in a compressed and deployed state, it may still be prone to damage when subjected to an external load. As such it may be less suitable for application in peripheral vessels and arteries, for instance those in the limbs and abdominal region of a human body, which lack substantial protection by the skeleton.

SUMMARY OF THE INVENTION

It is an object of the present invention to provide an expandable intraluminal endoprosthesis of the kind referred to in the opening paragraph with an improved ability to withstand external forces such that it is suitable for application in said peripheral vessels.

To this end, an expandable intraluminal endoprosthesis of the type described in the opening paragraph is, according to the present invention, characterized in that at least a part of said wall of said tubular member comprises, at least one substantially continuous winding of mutually staggered primary undulations advancing substantially helically along a longitudinal axis of said tubular member, in that a first primary undulation is connected to an associated second primary undulation by means of a first connection element, in that a third primary undulation subsequent to said first primary undulation is connected to an associated fourth primary undulation subsequent to said second primary undulation by means of a second connection element, and in that said first and second connection elements are mutually connected by means of a connection strut which lies interposed between said primary undulations, at least in said first unexpanded state. The additional material delivered by the connection strut gives the device more rigidity in the deployed state. This is especially predominant in a preferred embodiment of the endoprosthesis which according to the invention is characterized in that primary undulations are mutually interconnected by means of a number of connection elements which are regularly distributed over a helical turn of said at least one winding and in that a connection strut is present from each connection element within said turn to a subsequent connection element within said turn. In a sense, these connection struts between connection elements provide a secondary scaffolding pattern in the deployed state of the device, additional to the primary scaffolding by the winding(s) of primary undulations. By placing the connection elements and the connection struts at regular intervals with respect to each other, this secondary scaffolding will consist of a continuous helical winding advancing in between the primary undulations. As a result the structure features an enhanced hoop strength and an improved stent-to-vessel ratio in its deployed state, which renders the device particularly suitable in peripheral vessels and arteries where it is likely to be subjected incidentally to considerable external loads.

In order to allow a large radial expandability as well as expanded flexibility, a special embodiment of the endoprosthesis according to the invention is characterized in that the connection strut comprises a sub-structure of mutually staggered secondary undulations, at least in a crimped state of the device, lying in between subsequent turns of primary undulations. Accordingly the sub-structure formed by these undulations may be stretched so as to give way to the radial expansion of the device as a whole. Moreover, the stretching capability of the secondary undulations offers an improved flexibility of the device both in a crimped as well as in a deployed state. The latter feature contributes to an excellent capability of the device to conform itself to the natural anatomy of the body lumen in which it is to be implanted.

A further special embodiment of the endoprosthesis according to the invention is characterized in that the secondary undulations have an amplitude substantial equal to half the longitudinal pitch of said turns. In this manner the second undulations bridge the gap between both windings of primary undulations at least to the largest possible extent, which gives rise to an optimal stent-to-vessel ratio in the expanded state.

Still a further special embodiment of the endoprosthesis according to the invention is characterized in said primary undulations have a mutual pitch which is at least locally substantially an integer multiple of the mutual pitch of said secondary undulations. Thus it is possible to arrange the secondary undulations in phase with the primary undulations in order to obtain a regular structure. This structural regularity translates to highly predictable expansion characteristics.

A further special embodiment of the endoprosthesis according to the invention is characterized in that the connection elements comprise at least one tertiary undulation which lies embedded in said substructure of mutually staggered secondary undulations of said connection struts, at least in said first, unexpanded state of the device. Like the secondary undulations, said tertiary undulation provides for an enhanced radial expandability of the device, By embedding the tertiary undulation in the same substructure which is formed by the second undulations a substantially continuous secondary scaffolding structure is realized in the device, interposed between the primary undulations.

A further embodiment of the endoprosthesis according to the invention is characterized in that at least a part of said wall of said tubular member comprises at least two substantially continuous windings of mutually staggered primary undulations, advancing mutually substantial parallel along the longitudinal axis of said tubular member, in that a first winding comprises said first and third undulation, in that a second winding comprises said second and fourth undulation, and in that the connection struts are interposed in between both said windings. This embodiment features a dual-helix structure provided by both said windings with interposed connection elements and connection struts. Upon expansion of this device the interposed substructure will re-orientate itself with respect to the longitudinal axis of the device such that the connection elements will turn substantially traverse to said axis whereas the connection struts will assume a more parallel orientation with respect to said axis. As a result pairs of connection elements may form discrete ring like elements substantially traverse to the axis of the body interconnecting both windings, in the deployed state of the device. These ring like elements are themselves interconnected by substantially longitudinally orientated connection struts. These bonds together give rise to excellent scaffolding properties and stent-to-vessel ratio of the device once it has been deformed to an expanded state, whereas the structure remains extremely flexible both in a crimped as well as in an expanded state. The total structure as a result features an outstanding hoop strength and stent-to-vessel ratio in the deployed state without compromising its crimped and deployed flexibility.

In a further preferred embodiment the endoprosthesis according to the invention is characterized in that said structure comprises a substantial continuous filament which has been separated from a tube wall, in that said connection elements are an integral extension of the primary undulations which they interconnect and in that the connection strut is an integral extension of the connection elements thereby connected. The filament may be formed by applying computer controlled laser cutting or another high precision technique to a solid tube. Thus the device may be formed in any configuration without introducing any stress in the structure.

BRIEF DESCRIPTION OF THE DRAWINGS

The invention will now be further elucidated with reference to an illustrative example and an accompanying drawing in which.

This figure is drawn purely schematically and not everywhere to scale. Instead, some dimensions may be exaggerated for the sake of clarity. Like elements are provided with same reference numerals as much as possible.

DESCRIPTION OF THE PREFERRED EMBODIMENTS

Figure 1:
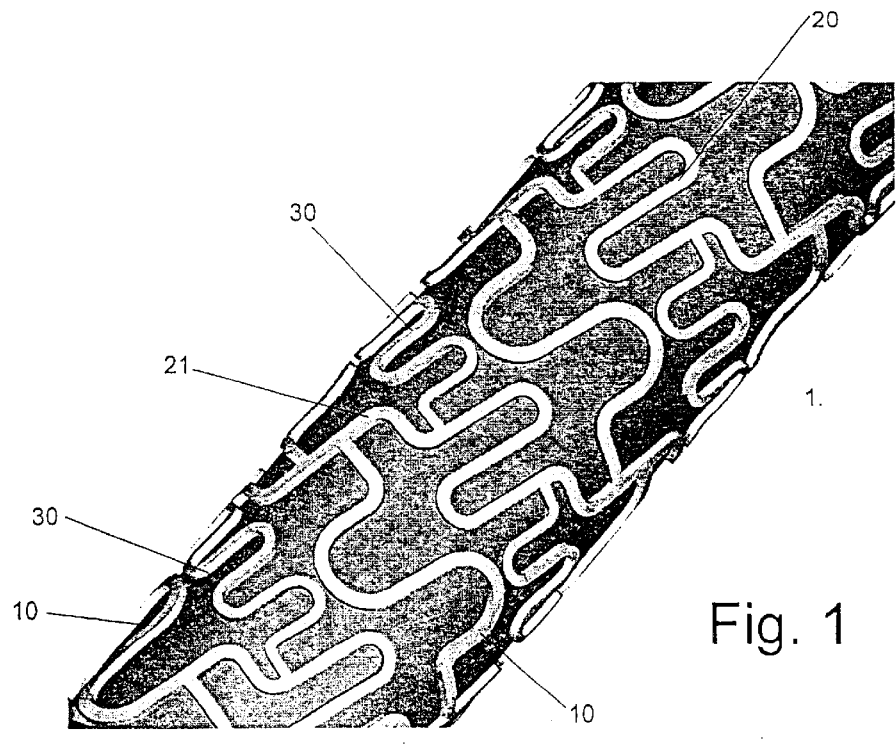
FIG. 1 represents an isometric view of a centre part of an embodiment of the endoprosthesis according to the present invention.

The intraluminal endoprosthesis shown in FIG. 1, a so called stent, comprises a substantially tubular member having a first and second end beyond the extremities of the drawing. A wall surface 1 is disposed in between these ends of the member of which a central module part is depicted in FIG. 1. Outside the drawing limits, this central module of repeating elements runs over in intermediate sections at both sides, which intermediate sections separate the centre module from end modules at opposite sides of the device. The basic difference between the different portions resides in the number of connection elements between adjacent undulations of the helical advancing pattern of the device, all as described in the co-pending application by applicant, which is incorporated herein by reference.

The wall surface 1 with its specific helical pattern has been cut or other wise liberated out of a solid tube wall of a tube of nitinol (NiTi) or any other suitable, bio-compatible material as described in the co-pending application by applicant. The wall surface of the stent is capable of acquiring a first crimped or unexpanded state which permits intraluminal delivery of the member into a lumen of a body passageway, particularly a blood vessel, as well as of second, expanded or deployed state upon exertion of a radially outwardly extending force to expand the lumen of the body passageway. The state shown corresponds to the first, crimped state, as it is manufactured. The radially outwardly extending force may be imposed on the device by means of a so called balloon tipped catheter which is received within the member and then inflated. Alternatively said force may be an intrinsic spring force of the device which is released by removing a sleeve from the device which initially covers it to confine the device in the crimped state. The first type of stent is generally referred to as a balloon-expandable stent, while the other stent is usually addressed as being self-expandable. The present embodiment focusses on the first type of stent, although it will be appreciated that the invention is also applicable to a self-expandable stent.

The structure making up the wall surface 1 of the member, at least in the depicted part of the device, essentially consists of a substantially continuous winding 10 of mutually staggered primary undulations 11–14, which advances substantially helically along a longitudinal axis of the tubular member. Adjacent primary undulations 11–14 from subsequent turns of said winding 10 are thereby mutually interconnected by means of connection elements 21,22,23 which bridge the gap between the respective turns. The connection elements 21,22,23 each comprise a s-curved bent 20 which greatly enhances the radial expandability of the device once it transforms from the crimped to the deployed state. Instead of connection elements 21,22,23 of the kind shown here, also otherwise devised connection elements may be used as described in the aforementioned co-pending application, just to suit the specific demands and desired characteristics of the device.

Figure 2:
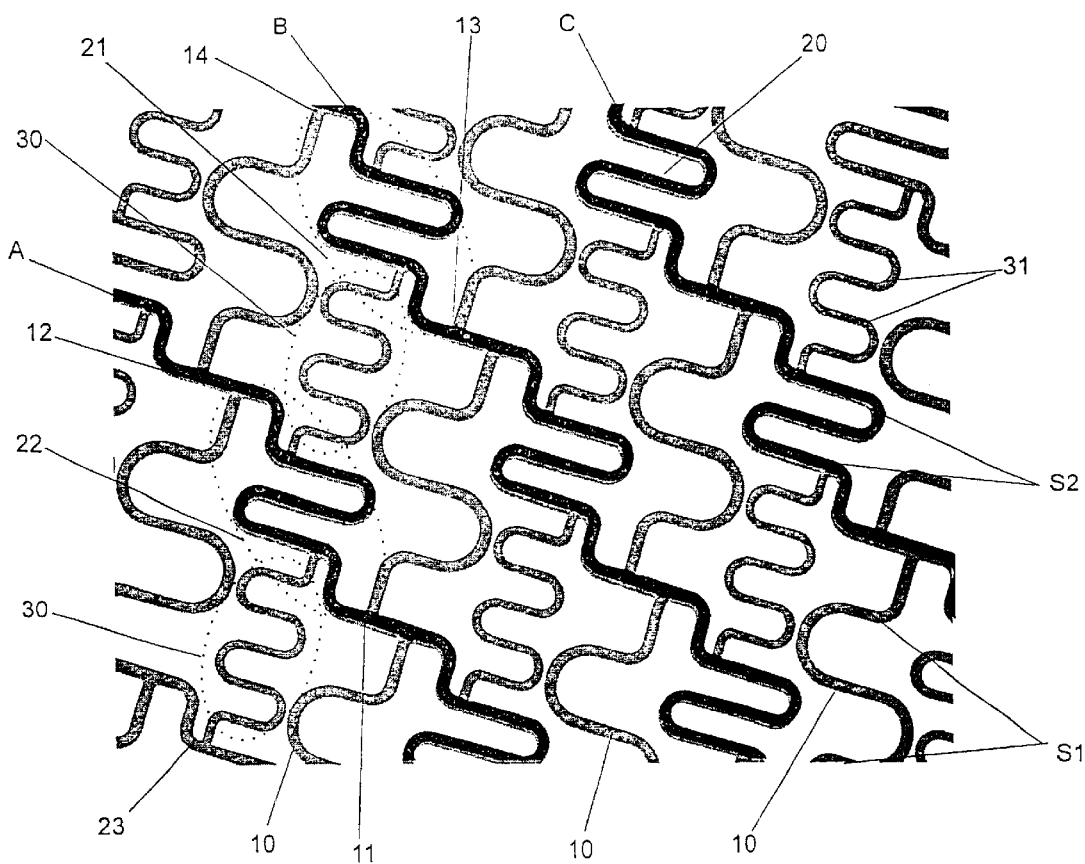
FIG. 2 shows a plan view of the device of FIG. 1 when cut and folded open.

For more detail concerning the interconnections within the structure, reference is made to FIG. 2 which shows the structure of FIG. 1 in plan view after it has been cut and folded open. As can be seen, each time a first primary undulation 11 is connected to an associated second primary undulation 12 by means of a first connection element 22, while a third primary undulation 13 subsequent to the first one 11 is connected to a fourth primary undulation 14 subsequent to the second one 12 by means of a second connection element 21. To enhance the overall stent-to-vessel ratio of the device and, more importantly, its hoop strength, the first and second connection elements 21, 22 are themselves interconnected by means of a connection strut 30 which lies interposed in between turns of the primary undulations 11–14. The connection strut 30 comprises a sub-structure of mutually staggered secondary undulations 31 which allow for a sufficient radial expandability of the device.

The second connection element 22 is likewise connected to a subsequent further connection element 23 by means of a further connection strut 30, such that the S-curved bents 20 of the connection elements 21,22,23 each form a kind of tertiary undulation lying embedded and integrated in said sub-structure of secondary undulations 31. This pattern continues along the helical path set by the winding 10 of primary undulations 11–14 such that a highly regular substructure is obtained of secondary undulations 31 and tertiary undulations 20 in between the primary undulations 11–14. In this case three connection elements 21,22,23 are applied per helical turn of the primary undulations 11–14. As a result three spines A,B,C may be distinguished in the structure advancing contra-helical to the winding 10 of primary undulations 11–14. These spiral spines A,B,C together with the winding 10 of primary undulations 11–14 create a double helix structure which results in an excellent hoop strength once it has been deployed. The winding 10 of primary undulations 11–14 is responsible for a major scaffolding within the structure while the spines A,B,C provide for minor scaffolding in the other helical direction. Both structures intersect at the primary undulations 11–14 interconnected by connection elements 21,22.

The mutual pitch s1 of the primary undulations 11–14 is approximately equal to an integer multiple of the pitch s2 of the undulations in the substructure of secondary- and tertiary undulations 20,31 to nicely accommodate said sub-structure. Also the amplitude of the secondary undulations 31 is taken to be about half the longitudinal pitch p of the turns of primary undulations 11,14. This amplitude leads to an optimal stent to vessel ratio of the device as the gap in between said turns is almost entirely filled with the pattern defined by the substructure of secondary undulations.

Because the entire structure is cut from a tube wall by means of laser cutting or a similar technique, the structure in fact comprises a continuous, coherent filament. The connection elements are an integral extension of the primary undulations which they interconnect and likewise are the connection struts an integral extension of the connection elements thereby interconnected. The pattern, width and form of said filament may be precisely controlled and is realized by means of a computer aided technique. A designer has hence an extremely great freedom of tailoring the device to suit the desired characteristics without introducing stress or other mechanical compromises in the structure. As such the connection struts 30 have been given a smaller filament width than the primary undulations 11–14, in order to gain flexibility, both in the crimped as in the expanded state, In this example, these widths are respectively approximately 0,15 and 0,20 mm. The connection elements 21,22,23 have an intermediate width of about 0,18 mm.

In practice the device is positioned on the balloon of a balloon tipped catheter and guided with the catheter through the lumen of the body to the stenosis to be treated. At this location the balloon is inflated in order to expand the stent device to the required diameter in order to re-establish a sufficient blood passageway in the vessel. This expanded diameter will be somewhat larger than the natural diameter of the vessel in order to allow for natural tissue growth over the stent body without compromising the blood flow through the vessel. After expansion of the stent, the catheter is retracted leaving the implanted stent in position. Due to said tissue growth the stent will eventually lie substantially embedded in the vessel wall, while giving it continuous support.

Due to the helical pattern of the device, void of any discontinuities, and the great number of undulations within the structure, the overall device is extremely flexible both in the crimped as in the expanded state. Moreover the device of the invention is highly conformal to the natural course of the vessel to be treated and accordingly nicely fits to provide an evenly distributed support. The connection struts give the structure more coherence which results in an extremely well hoop strength, making the device especially suitable for the treatment of peripheral vessels which are relatively prone to sudden external loads.

Although the invention has been described hereinbefore with reference to merely a single embodiment it will be appreciated that the invention is by no means limited to this specific example. Within the scope of the invention many other embodiments and variations are on the contrary feasible for a skilled practitioner. As such he may use different amplitudes, pitches and patterns to tailor the device to a specific application. Also the number of helical windings of primary undulations may be larger than only a single one. Especially one or more parts of the device may comprise for instance two substantially continuous windings of mutually staggered primary undulations, advancing mutually substantial parallel along the longitudinal axis of said tubular member, A first one of those windings may then comprise said first and third undulation, while the other one comprises said second and fourth undulation. In case the connection elements are regularly distributed in between said windings and all mutually interconnected by connection struts the resulting, expanded structure will feature ring-like elements formed by the connection struts which are longitudinally interlinked buy the helically advancing primary undulations. This structure is capable to a high conformability to the natural vessel course whilst having a large radial stiffness or hoop strength.

What is claimed is:

1. An expandable intraluminal endoprosthesis comprising:

a tubular member having a first and second end and a wall surface disposed between said first and second end, the wall having a first diameter in a first, unexpanded state which permits intraluminal delivery of the member into a lumen of a body passageway and being capable of acquiring a second diameter in an expanded and deformed state upon the exertion of a radially outwardly extending force to expand the lumen of the body passageway, wherein at least a part of said wall of said tubular member comprises, at least one substantially continuous winding of mutually staggered primary undulations advancing substantially helically along a longitudinal axis of said tubular member, a first primary undulation being connected to an associated second primary undulation by means of a first connection element, a third primary undulation subsequent to said first primary undulation being connected to an associated fourth primary undulation subsequent to said second primary undulation by means of a second connection element, and wherein said first and second connection elements are mutually connected by means of a connection strut which lies interposed between said primary undulations, at least in said first unexpanded state, wherein said connection strut has a smaller filament width than the primary undulations.

2. The endoprosthesis according to claim 1, wherein the connection strut comprises a sub-structure of mutually staggered secondary undulations, at least in a crimped state of the device, lying in between subsequent turns of primary undulations.

3. The endoprosthesis according to claim 2, wherein said primary undulations have a mutual pitch which is at least locally substantially an integer larger than one multiple of the mutual pitch of said secondary undulations.

4. The endoprosthesis according to claim 3, wherein the secondary undulations have an amplitude substantial equal to half the longitudinal pitch of said turns.

5. The endoprosthesis according to claim 2, wherein the connection elements comprise at least one tertiary undulation which lies embedded in said substructure of mutually staggered secondary undulations of said connection struts, at least in said first, unexpanded state of the device.

6. The endoprosthesis according to claim 1, wherein at least a part of said wall of said tubular member comprises at least two substantially continuous windings of mutually staggered primary undulations, advancing mutually substantial parallel along the longitudinal axis of said tubular member, in that a first winding comprises said first and third undulation, in that a second winding comprises said second and fourth undulation, and in that the connection struts are interposed in between both said windings.

7. The endoprosthesis according to claim 1, wherein the tubular member comprises a substantial continuous filament which has been separated from a tube wall, in that said connection elements are an integral extension of the primary undulations which they interconnect and in that the connection strut is an integral extension of the connection elements thereby connected.

8. A tubular, expandable intraluminal endoprosthesis comprising:

plural undulating spines that each advance helically to form a tubular member, each of said spines having alternating first and second sections, the first sections having undulations and the second sections being substantially linear;

plural undulating first connections that connect adjacent ones of said spines at respective ones of said first sections;

plural undulating second connections that connect adjacent ones of said spines at respective ones of said second sections, said first connections alternating with said second connections, wherein each undulation in said first connections has an amplitude and a pitch that are substantially smaller than a respective amplitude and pitch of undulations in said second connections.

9. The endoprosthesis of claim 8, wherein said first connections are serially connected but separated from each other by the undulations of a respective ones of said first sections.

10. The endoprosthesis of claim 8, wherein said first connections have a smaller width than said second connections.

11. The endoprosthesis of claim 8, wherein each undulation in said first sections has a pitch that is substantially smaller than the pitch of undulations in said second connections and an amplitude that substantially the same as the amplitude of undulations in said second connections.

12. The endoprosthesis of claim 11, wherein each undulation in said first sections has a pitch that is about one-half the pitch of undulations in said second connections.

13. The endoprosthesis of claim 8, wherein the pitch and amplitude of each undulation in said first connections is about one-half the amplitude and pitch of undulations in said second connections.

14. A tubular, expandable intraluminal endoprosthesis comprising:

a first helical member with undulations having a first pitch and a first amplitude; and a second helical member with undulations having a second pitch substantially smaller than the first pitch, said second helical member having first alternating first and second sections, said first sections having the first amplitude and said second sections having a second amplitude substantially smaller than the first amplitude, said first and second helical members alternating to form a tubular member, wherein said first sections of said second helical members are connected by plural connecting members that extend transversely through said first helical member.

15. The endoprosthesis of claim 14, wherein said first sections of said second helical members and said plural connecting members form a continuous spine that extends helically in a direction transverse to a direction of said first and second helical members.

16. The endoprosthesis of claim 14, wherein said second sections of said second helical member have a smaller width than said first helical member.

17. The endoprosthesis of claim 14, wherein the first pitch is about twice the second pitch.

18. The endoprosthesis of claim 14, wherein the first amplitude is about twice the second amplitude.

* * * * *